(12) United States Patent
Jiang et al.

(10) Patent No.: US 11,850,174 B2
(45) Date of Patent: Dec. 26, 2023

(54) DELIVERY APPARATUS AND SYSTEM

(71) Applicant: Shenzhen Lifetech Endovascular Medical Co., Ltd., Shenzhen (CN)

(72) Inventors: Wei Jiang, Shenzhen (CN); Feng Peng, Shenzhen (CN); Benhao Xiao, Shenzhen (CN); Gang Wang, Shenzhen (CN); Kui Liu, Shenzhen (CN)

(73) Assignee: Lifetech Scientific (Shenzhen) Co, Ltd., Shenzhen (CN)

( * ) Notice: Subject to any disclaimer, the term of this patent is extended or adjusted under 35 U.S.C. 154(b) by 141 days.

(21) Appl. No.: 17/418,637

(22) PCT Filed: Oct. 31, 2019

(86) PCT No.: PCT/CN2019/114680
§ 371 (c)(1),
(2) Date: Jun. 25, 2021

(87) PCT Pub. No.: WO2020/134538
PCT Pub. Date: Jul. 2, 2020

(65) Prior Publication Data
US 2022/0117764 A1    Apr. 21, 2022

(30) Foreign Application Priority Data

Dec. 27, 2018  (CN) .......................... 201811613310.5
Dec. 27, 2018  (CN) .......................... 201811613311.X

(51) Int. Cl.
*A61F 2/966* (2013.01)
(52) U.S. Cl.
CPC .................................... *A61F 2/966* (2013.01)
(58) Field of Classification Search
CPC .... A61F 2/966; A61F 2/07; A61F 2002/9511; A61F 2002/9665
See application file for complete search history.

(56) References Cited

U.S. PATENT DOCUMENTS

2001/0044648 A1* 11/2001 Wolinsky .................. A61F 2/95
                                                                623/1.1
2002/0082674 A1*  6/2002 Anson ....................... A61F 2/07
                                                               623/1.33
(Continued)

FOREIGN PATENT DOCUMENTS

CN         101045022 A      10/2007
CN         101357088         2/2009
(Continued)

OTHER PUBLICATIONS

Office Action dated Dec. 1, 2021 for corresponding China Application No. 201811613310.5.
(Continued)

*Primary Examiner* — Richard G Louis
(74) *Attorney, Agent, or Firm* — Raymond Sun

(57) ABSTRACT

A delivery apparatus includes a sheath assembly, a tip, and a handle assembly. The sheath assembly includes an inner core tube, a push tube surrounding and receiving the inner core tube, and a sheath surrounding and receiving the push tube and capable of moving axially relative to the push tube. The tip is connected to the distal end of the inner core tube. The handle assembly is connected to the proximal end of the sheath. A tube cavity channel for the inner core tube to extend through is provided within the push tube. A guide wire channel also is provided in the push tube. A limiting mechanism is provided on the tip and is used for being detachably connected to a guide wire extending through the guide wire channel.

19 Claims, 10 Drawing Sheets

(56) References Cited

U.S. PATENT DOCUMENTS

| | | | |
|---|---|---|---|
| 2004/0082935 A1* | 4/2004 | Lee | A61M 25/0029 604/523 |
| 2006/0100694 A1* | 5/2006 | Globerman | A61F 2/856 623/1.35 |
| 2008/0082158 A1 | 4/2008 | Tseng et al. | |
| 2008/0264102 A1* | 10/2008 | Berra | A61F 2/966 623/1.15 |
| 2009/0099640 A1* | 4/2009 | Weng | A61F 2/95 623/1.11 |
| 2012/0232635 A1* | 9/2012 | Jensen | A61F 2/95 156/84 |
| 2013/0289713 A1 | 10/2013 | Pearson et al. | |
| 2016/0374842 A1 | 12/2016 | Havel et al. | |

FOREIGN PATENT DOCUMENTS

| | | |
|---|---|---|
| CN | 102961198 A | 3/2013 |
| CN | 108236533 A | 7/2018 |
| CN | 108245290 A | 7/2018 |
| CN | 108261252 A | 7/2018 |
| CN | 109700564 A | 5/2019 |
| CN | 109700565 A | 5/2019 |
| CN | 109700565 B | 7/2021 |
| EP | 2436343 B1 | 2/2017 |
| EP | 3292844 A1 | 3/2018 |
| EP | 2066270 A1 | 6/2019 |

OTHER PUBLICATIONS

International Search Report dated Jan. 23, 2020 for corresponding PCT Application No. PCT/CN2019/114680.
Response to Office Action dated Feb. 10, 2021 for corresponding China Application No. 201811613311.X.
Translation of Response to Office Action dated Feb. 10, 2021 for corresponding China Application No. 201811613311.X.
Notification of Grant for corresponding China Application No. 201811613311.X.
Translation of Notification of Grant for corresponding China Application No. 201811613311.X.
Office Action dated Feb. 10, 2021 for corresponding China Application No. 201811613311.X.
Translation of Office Action dated Feb. 10, 2021 for corresponding China Application No. 201811613311.X.
European Search Report dated Aug. 30, 2022 for corresponding European Application No. EP 19 90 5560.
Office Action dated Aug. 5, 2022 for corresponding Indian Application No. 202127032648.

* cited by examiner

DELIVERY APPARATUS AND SYSTEM

FIELD

The application relates to the field of interventional medical instruments, in particular to a delivery apparatus and system.

BACKGROUND

In the past ten years, the endovascular graft exclusion of an aorta by a covered stent has been widely used in lesions such as arterial aneurysms and aortic dissections of thoracic and abdominal aortas and the like, and has become a first-line therapy due to its definite therapeutic effect, minimal trauma, fast recovery and fewer complications. However, the positioning accuracy of the delivery system in the prior art is not good, and the conventional delivery systems cannot release a covered stent accurately and quickly. Therefore, there is a need to design a reliable delivery system.

SUMMARY

The problem to be solved is to provide a delivery apparatus and system aimed at the defects described in background.

A solution adopted by the present application for solving the problem is as follows.

A delivery apparatus is provided, including a sheath assembly, a tip, and a handle assembly. The sheath assembly includes an inner core tube, a push tube surrounding and receiving the inner core tube, and a sheath surrounding and receiving the push tube and capable of moving axially relative to the push tube; the tip is connected to a distal end of the inner core tube; the handle assembly is connected to a proximal end of the sheath; a tube cavity channel for the inner core tube to extend through is provided within the push tube; a guide wire channel also is provided in the push tube; a limiting mechanism is provided on the tip; and the limiting mechanism is used for being detachably connected to a guide wire running through the guide wire channel.

The present application further provides a delivery system, including a tube cavity stent, and the above-mentioned delivery apparatus. The tube cavity stent includes a tubular main body, and a semi-releasing apparatus connected to a surface of the tubular main body; the semi-releasing apparatus includes a limiting guide wire, and a restraint unit movably connected to the limiting guide wire and used for performing circumferential restraining on the tubular main body; the limiting guide wire extends through the guide wire channel; and the limiting guide wire is detachably connected to the limiting mechanism.

The present application further provides a delivery system, including a tube cavity stent, and the above-mentioned delivery apparatus. The tube cavity stent includes a tubular main body, and at least one branch connected to the tubular main body; a preset guide wire is arranged in the branch; the preset guide wire extends through the guide wire channel; and the preset guide wire is detachably connected to the limiting mechanism.

The application further provides a delivery system, including a tube cavity stent, and the above-mentioned delivery apparatus. The tube cavity stent includes a tubular main body, at least one branch connected to the tubular main body, and a semi-releasing apparatus connected to a surface of the tubular main body; the semi-releasing apparatus includes a limiting guide wire, and a restraint unit movably connected to the limiting guide wire and used for circumferential restraint the tubular main body; a preset guide wire is arranged in the branch; the preset guide wire and the limiting guide wire respectively extend through the guide wire channel; and the preset guide wire and/or the limiting guide wire is detachably connected to the limiting mechanism.

The present application further provides a delivery apparatus, including a sheath assembly, and a handle assembly connected to a proximal end of the sheath assembly. The sheath assembly includes an inner core tube, a push tube surrounding and receiving the inner core tube, and a sheath surrounding and receiving the push tube and capable of moving axially relative to the push tube; a tube cavity channel for the inner core tube to extend through is provided within the push tube; the sheath assembly further includes a supporting member located in the tube cavity channel, and a length of the supporting member is not greater than a length of the push tube.

The present application further provides a delivery system, including a tube cavity stent, and characterized by further including the above-mentioned delivery apparatus.

In view of the above, implementation of the delivery apparatus and system of the present application has the following advantageous effects: in the present application, the guide wire channel used for the guide wire to extend through is provided within the push tube of the delivery apparatus, and the limiting mechanism detachably connected to the guide wire is arranged on the tip, and can ensure that the guide wire is always connected to the limiting mechanism during the delivery process, thereby preventing the guide wire from shifting and affecting the overall positioning precision of the system.

BRIEF DESCRIPTION OF THE DRAWINGS

The present application will be further described with reference to the accompanying drawings and embodiments. In the drawings.

DETAILED DESCRIPTION OF THE EMBODIMENTS

In order to make the above objectives, features and advantages of the present application more obvious and understandable, specific implementation modes of the present application are described in detail below with reference to the accompanying drawings. In the following descriptions, numerous specific details are set forth in order to provide a thorough understanding of the present application. However, the present application may be embodied in many different forms than those herein set forth, and similar modifications may be made by those skilled in the art without departing from the essence of the present application, thus the present application should not be limited by the following disclosed specific implementations.

It should be noted that when an element is referred to as being "fixed" or "arranged" to another element, it can be directly on another element or an intermediate element may also exist. When an element is referred to as being "connected" to another element, it can be directly connected to another element or an intermediate element may also exist. The terms "vertical", "horizontal", "left", "right" and similar expressions used herein are only for the purpose of explanation, and do not denote the unique implementation mode.

Unless defined otherwise, all technical and scientific terms used herein have the same meaning as commonly understood by those of ordinary skill in the art to which the present application belongs. The terms used in the description of the present application is for the purpose of describing specific implementation modes only and are not intended to limiting the present application. As used herein, the term "and/or" includes any and all combinations of one or more of the associated listed items.

In the interventional medical field, an end, close to an operator, of an instrument is usually defined to be a proximal end, and an end away from the operator is defined to be a distal end.

Figure 1:
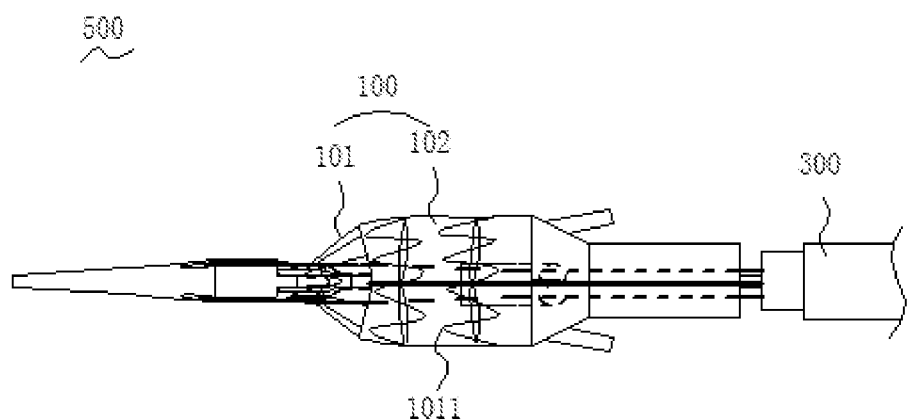
FIG. 1 is a schematic diagram of a delivery system provided by the present application.

Referring to FIG. 1, the present application provides a delivery system 500, including a tube cavity stent 100 and a delivery apparatus 300 cooperating with the tube cavity stent 100.

The tube cavity stent 100 includes a bare stent 101 and a cover film 102 connected to the bare stent 101. The tube cavity stent 100 is of a hollow lumen structure, and a tube cavity of the tube cavity stent 100 forms a channel for the flow of blood flow.

The bare stent 101 is made of a material with good biocompatibility, such as nickel titanium and stainless steel. The cover film 102 is made of a polymer material with good biocompatibility, such as PTFE, FEP and PET. The bare stent 101 includes a plurality of turns of waveform rings 1011; each turn of a waveform ring 1011 includes a plurality of wave crests, a plurality of wave troughs and a plurality of connection rods respectively connected to adjacent wave crests and wave troughs; and the plurality of turns of waveform rings 1011 are sequentially arranged from a proximal end to a distal end and are preferably arranged in parallel at intervals. The waveform ring 1011 is of a closed cylindrical structure, and the plurality of turns of waveform rings 1011 may have the same or similar wave shapes. For example, the waveform ring 1011 may be of a Z-shaped wave, M-shaped wave, V-shaped wave, sinusoidal wave structure, or other structures that may be radially compressed to a very small diameter. It can be understood that the present embodiment does not define the specific structure of the waveform ring 1011, and the waveform of the waveform ring 1011 may be set as required. In addition, both the number of waveforms in each turn of waveform ring 1011 and the waveform height may be set as required. In actual preparation, the bare stent 101 is woven by nickel-titanium wires or formed by cutting and shaping a nickel-titanium tube, and then the cover film 102 is fixed on a surface of the bare stent 101 via suturing or high-temperature pressing.

Figure 2:
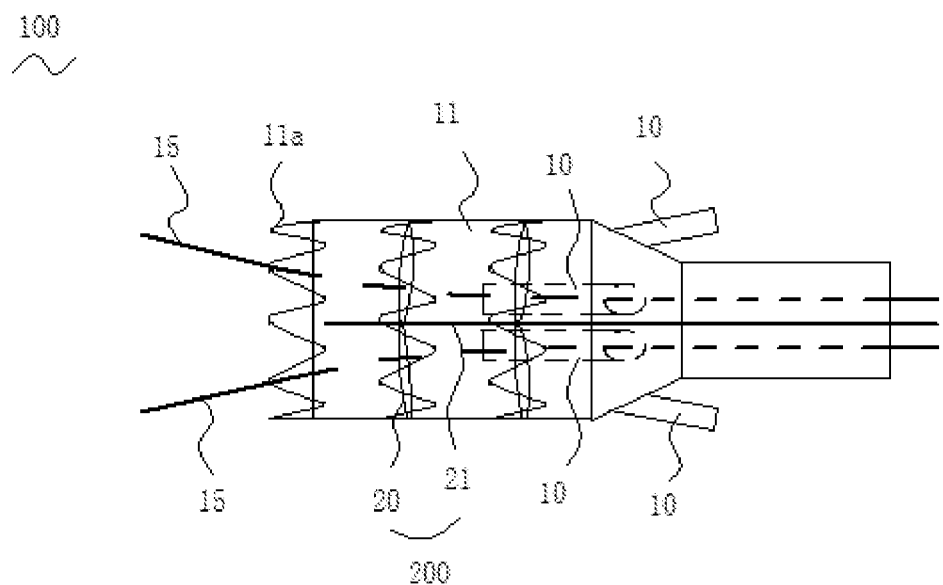
FIG. 2 is a schematic diagram of a tube cavity stent of the delivery system shown in FIG. 1.

Referring to FIG. 2, the tube cavity stent 100 includes a tubular main body 11, and a semi-releasing apparatus 200 connected to the tubular main body 11. The semi-releasing apparatus 200 includes a limiting guide wire 21, and a restraint unit 20 movably connected to the limiting guide wire 21 and providing circumferential restraint on the tubular main body 11. After the tube cavity stent 100 is released from the delivery apparatus 300, the tube cavity stent 100 is in a semi-released state under the restraint of the semi-releasing apparatus 200; at this time, the tube cavity stent 100 does not fit to a vascular wall, and an operator can still adjust the axial and circumferential positions of the tube cavity stent 100; after accurate positioning, the limiting guide wire 21 is separated from the restraint unit 20 to relieve the restraint of the semi-releasing apparatus 200, so that the tube cavity stent 100 expands and fits against the wall.

The tubular main body 11 is connected with at least one branch 10 communicating with the tubular main body 11. The branch 10 may be an inner branch, or an outer branch. A preset guide wire 15 is provided within the at least one branch 10, and the preset guide wire 15 extends through the branch 10. After the delivery apparatus 300 is withdrawn from a body, the preset guide wire 15 is still retained in the branch 10; at this time, the preset guide wire 15 can be captured by a guide wire capture device (not shown) from a distal end 11a of the tubular main body 11. An end of the preset guide wire 15 is captured out of the body, and a blood vessel channel from the outside of the body to the branch 10 is built by using the guide wire 15. Then, one end of an extending stent (not shown) is inserted into the branch 10 through this channel, and the other end of the extending stent is located into a branch vessel. In the embodiment shown in FIG. 2, there are four branches 10: two inner branches and two outer branches. The preset guide wires 15 are respectively provided within the two inner branches.

Figure 3:
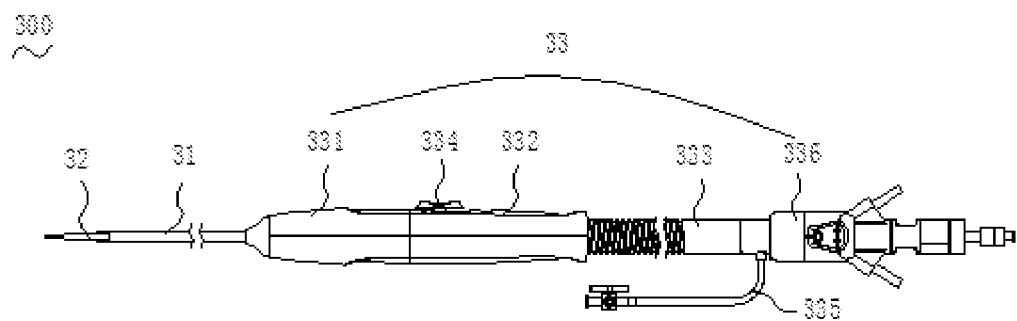
FIG. 3 is a schematic diagram of a delivery apparatus of the delivery system shown in FIG. 1.

Referring to FIG. 3, the delivery apparatus 300 includes a sheath assembly 31, a tip 32 and a handle assembly 33. The tip 32 is connected to a distal end of the sheath assembly 31, and the tip 32 is a hollow structure, an inner cavity of which is communicated with a tube cavity of the sheath assembly 31 and serves as a guide wire channel. The handle assembly 33 is connected to a proximal end of the sheath assembly 31 and used for controlling axial movement of all parts of the sheath assembly 31 to release the tube cavity stent 100 from the delivery apparatus 300.

Figure 4:
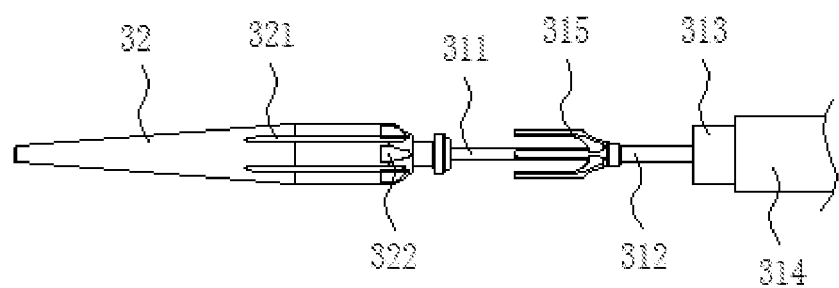
FIG. 4 is a schematic diagram of a sheath assembly of the delivery apparatus shown in FIG. 3.

Referring to FIG. 4, the sheath assembly 31 includes an inner core tube 311, an outer core tube 312, a push tube 313, a sheath 314 and a fixed anchor 315.

The tip 32 is connected to a distal end of the inner core tube 311, and a tube cavity of the inner core tube 311 is communicated with the inner cavity of the tip 32 to serve as the guide wire channel. The outer core tube 312 surrounds the inner core tube 311 and can move axially relative to the inner core tube 311; the fixed anchor 315 is connected to a distal end of the outer core tube 312, and moves axially with the outer core tube 312. The tip 32 is provided with a fixed anchor limiting slot 322, and the fixed anchor 315 is detachably connected into the fixed anchor limiting slot 322. The push tube 313 surrounds the outer core tube 312, and is located between the outer core tube 312 and the sheath 314; the sheath 314 surrounds the push tube 313 and can move axially relative to the push tube 313; and the handle assembly 33 is connected to a proximal end of the sheath 314. When the sheath 314 surrounds the outer core tube 312, an annular cavity is formed between the sheath 314 and the outer core tube 312, and the compressed tube cavity stent 100 is accommodated in the annular cavity. Referring again to FIG. 1, the bare stent 101 at one end of the tube cavity stent 100 is hooked on the fixed anchor 315, and the other end of the tube cavity stent 100 abuts against a distal end surface of the push tube 313, so that the tube cavity stent 100 is axially compressed between the fixed anchor 315 and the push tube 313. Since the entire tube cavity stent 100 is restrained in the sheath 314, the tube cavity stent 100 and the delivery apparatus 300 can maintain a relative stationary state before the stent reaches a lesion position. After the delivery apparatus 300 loaded with the tube cavity stent 100 reaches the lesion position, the tube cavity stent 100 is released.

In use, the handle assembly 33 is first used to withdraw the sheath 314 to release the tube cavity stent 100 from the delivery apparatus 300; and at this time, under the restraint of the semi-releasing apparatus 200, the tube cavity stent 100 is in the semi-released state. Secondly, the axial and circumferential positions of the tube cavity stent 100 are adjusted; and after accurate positioning, the limiting guide wire 21 is separated from the restraint unit 20 to relieve the restraint of the semi-releasing apparatus 200, so that the tube cavity stent 100 expands and fits against a vessel wall. Then, the outer core tube 312 is withdrawn relative to the inner core tube 311, and the fixed anchor 315 follows the outer core tube 312 to withdraw and is gradually separated from the fixed anchor limiting slot 322, thereby relieving the restraint to the bare stent 101; and at this time, the tube cavity stent 100 completely expands. Finally, the delivery apparatus 300 is withdrawn from the body, and one end of the preset guide wire 15 in the branch 10 is captured out of the body through the guide wire capture device (not shown), and the blood vessel channel from the outside of the body to the branch 10 is built by using the preset guide wire. The extending stent is inserted into the branch 10.

Figure 5:
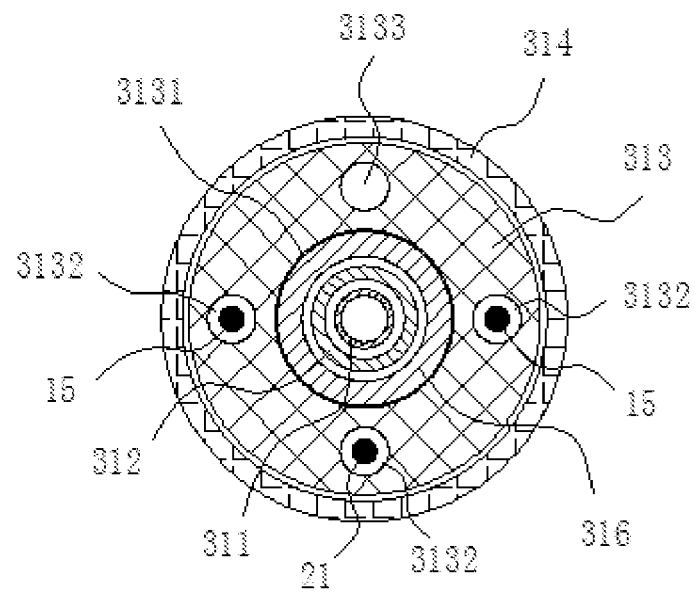
FIG. 5 is a cross-sectional view of a proximal end of the sheath assembly shown in FIG. 3.

In an actual surgical process, the distal end part of the sheath assembly 31 enters a human blood vessel, so its distal end needs to have enough flexibility, and the proximal end of the sheath assembly 31 needs to provide an enough supporting force to reduce a promotion power required by release of the tube cavity stent. Therefore, referring to FIG. 5, the sheath assembly 31 further includes a supporting member 316. The supporting member 316 is located in the push tube 313, and the length of the supporting member 316 is not greater than the length of the push tube 313. The supporting member 316 may be a relatively hard pipe fitting such as a metal tube. In the embodiment shown in FIG. 5, the supporting member 316 is of a hollow tubular structure, and is fixed on an inner wall of the push tube 313. A proximal end of the supporting member 316 extends to the proximal end of the push tube 313, and a distal end of the supporting member 316 extends to a distal end of the push tube 313. The supporting member 316 may be fixed in the push tube 313 via glue, hot melting or the like. It can be understood that the present embodiment does not define the specific structure of the supporting member 316. For example, in other embodiments, the supporting member 316 is a thin strip-type solid metal member, which is fixed on the inner wall of the push tube 313.

A tube cavity channel 3131 and a guide wire channel 3132 which extend through respectively in an axial direction are provided within the push tube 313. The supporting member 316 is fixed on an inner wall of the tube cavity channel 3131, and the outer core tube 312 extends through the tube cavity channel 3131. The limiting guide wire 21 and/or the preset guide wire 15 extend through the guide wire channel 3132. In the embodiment shown in FIG. 5, there are three guide wire channels 3132. The preset guide wires 15 extend through two of the three guide wire channels 3132, and the limiting guide wire 21 extends through the other one.

The limiting guide wire 21 and/or the preset guide wire 15 may be a metal guide wire having relatively low surface roughness and good human biocompatibility, such as a nickel-titanium wire. In order not to increase the entire contour size of the delivery system and avoid the limiting guide wire 21 and the preset guide wire 15 from being bent by a stress, the wire diameters of both the limiting guide wire 21 and the preset guide wire 15 are between 0.2 mm to 0.6 mm.

In order to avoid the distal ends of the limiting guide wire 21 and the preset guide wire 15 from damaging a blood vessel, the proximal end sections of the limiting guide wire 21 and the preset guide wire 15 are usually softer flexible sections. However, since the proximal end section of the preset guide wire 15 is softer, in the delivery process, the proximal end section of the preset guide wire 15 easily shifts. If the preset guide wire 15 passes through the bare stent 101 below the wave crests of the bare stent 101, after the bare stent 101 expands and is fitted against the vessel wall, the preset guide wire 15 may be squeezed between the bare stent 101 and the vascular wall, resulting in the possibility that the extending stent cannot be inserted.

Figure 6:
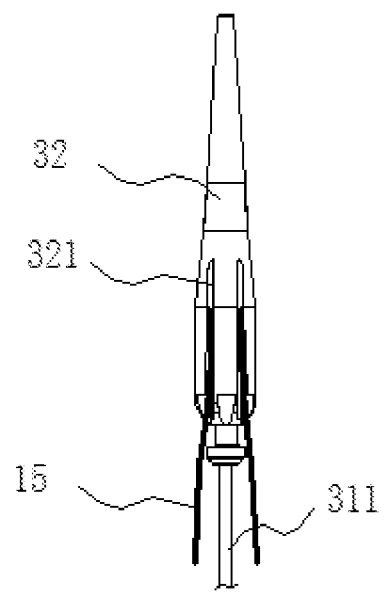
FIG. 6 is a schematic diagram of a first limiting mechanism of a tip of the delivery apparatus shown in FIG. 3.
Figure 7:
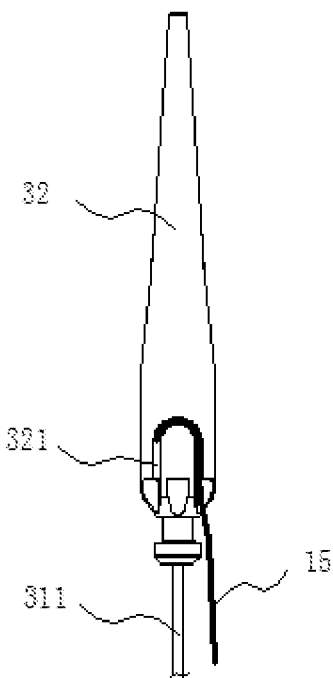
FIG. 7 is a schematic diagram of a second limiting mechanism of the tip of the delivery apparatus shown in FIG. 3.

Referring to FIG. 6, a limiting mechanism 321 is arranged on the tip 32, and the front ends of the limiting guide wire 21 and/or the preset guide wire 15 are detachably connected to the limiting mechanism 321. Under the action of an external force, the guide wires may be separated from the limiting mechanism 321. During assembly, the limiting guide wire 21 and/or the preset guide wire 15 passes through from the front end of the tube cavity stent 100, and the front ends of the limiting guide wire 21 and/or the preset guide wire 15 are connected to the limiting mechanism 321 to ensure that in the delivery process, the front ends of the limiting guide wire 21 and/or the preset guide wire 15 are always connected to the limiting mechanism 321. In the embodiment shown in FIG. 6, the limiting mechanism 321 is a limiting slot; the limiting slot extends in an axial direction of the tip 32 to the proximal end of the tip 32. The limiting guide wire 21 and/or the preset guide wire 15 are accommodated in the limiting slot and are in interference fit with the limiting slot. Under the action of an external force, the guide wires may be separated from the limiting slot. It can be understood that the present embodiment does not define the specific structure of the limiting slot. For example, in the embodiment shown in FIG. 7, the limiting slot is approximately a U-shaped slot; the front ends of the limiting guide wire 21 and/or the preset guide wire 15 extend to a bent section of the U-shaped slot to avoid the guide wires from falling off from the limiting slot. The limiting guide wire 21 and/or the preset guide wire 15 also may be in interference with the U-shaped slot to further avoid the guide wires from falling off from the limiting slot.

It also can be understood that the present embodiment does not define the specific structure of the limiting mechanism 321 as long as it is ensured that the limiting guide wire 21 and/or the preset guide wire 15 can be restrained on the limiting mechanism 321 and the guide wires may be separated, under the action of an external force, from the limiting mechanism 321. For example, in other embodiments, the limiting mechanism 321 is a clamping mechanism composed of two elastic sheets. The two elastic sheets are arranged at the tip, and the guide wires are clamped between the two elastic sheets. Under the action of an external force, the guide wires are separated from the two elastic sheets.

Referring again to FIG. 3, the handle assembly 33 includes a fixed handle 331, a sliding handle 332, a guide rod 333, a locking assembly 334, a communication tube 335 and a joint assembly 336.

The joint assembly 336 is connected to the proximal end of the sheath assembly 31; the communication tube 335 is connected to the joint assembly 336, and is communicated with the inner cavity of the sheath assembly 31. A proximal end of the guide rod 333 is fixedly connected to the joint assembly 336, and the fixed handle 331 is fixed at a distal end of the guide rod 333. The sliding handle 332 is slidably connected to the guide rod 333. The sliding handle 332 is fixedly connected to the sheath 314. The sheath 314 follows the sliding handle 332 to axially move. The locking assembly 334 is connected to the sliding handle 332 and the guide rod 333 respectively, and is used to control an axial relative movement between the sliding handle 332 and the guide rod 333. When the locking assembly 334 is in a locked state, the sliding handle 332 and the guide rod 333 cannot be moved relative to each other; and when the locking assembly 334 is in a unlocked state, the sliding handle 332 and the guide rod 333 can move relative to each other.

In the embodiment shown in FIG. 3, the guide rod 333 is slidably connected to the sliding handle 332 through a threaded structure. It can be understood that the present embodiment does not define the specific mode of the sliding connection between the guide rod 333 and the sliding handle 332 as long as they can slide relative to each other. For example, in other embodiments, a sliding rail can be arranged on the guide rod 333, and a sliding block slidably connected in the sliding rail is arranged on the sliding handle 332.

Figure 8:
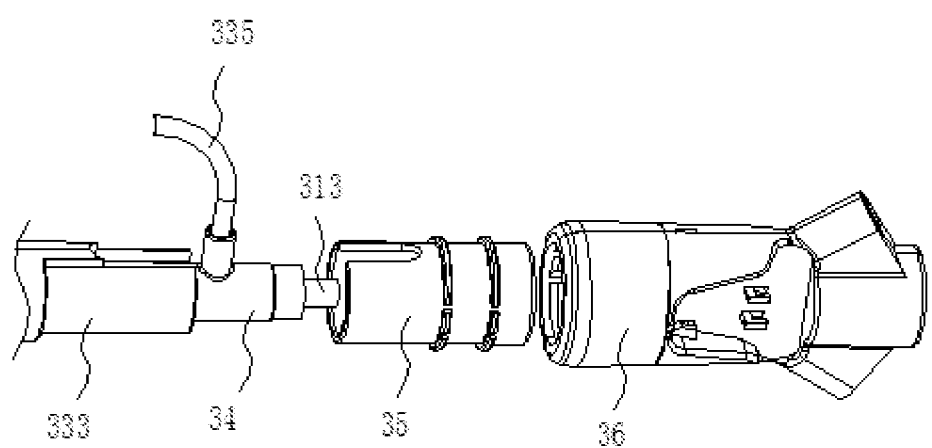
FIG. 8 is an exploded diagram of a joint assembly of the delivery apparatus shown in FIG. 3.

Referring to FIG. 8, the joint assembly includes a push tube joint 34, a guide rod joint 35 and a guide wire joint 36. The guide rod joint 35 is connected to the proximal end of the guide rod 333. The push tube joint 34 is fixed in the guide rod joint 35. The guide wire joint 36 is fixed outside the guide rod joint 35. The push tube joint 34 is fixed outside the push tube 313. The limiting guide wire and the preset guide wire in the push tube 313 respectively extend out of the handle assembly 33 through the guide wire joint 36.

Figure 9:
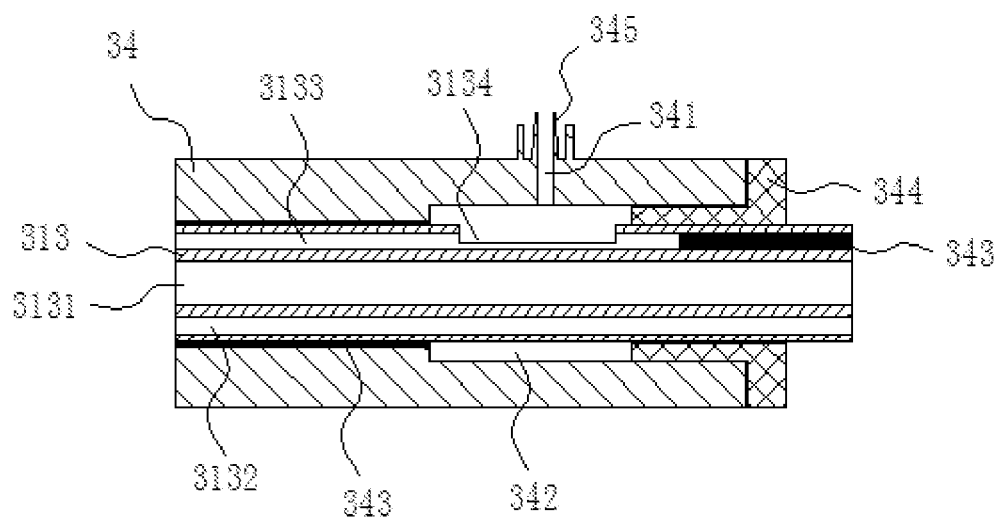
FIG. 9 is a sectional view of a push tube joint of the joint assembly shown in FIG. 8.

Referring to FIG. 9, an exchange channel 3133 distributed in the axial direction is provided within the push tube 313. The exchange channel 3133 is isolated from the tube cavity channel 3131 and the guide wire channel 3132, and is communicated with an external environment. A distal end of the exchange channel 3133 extends to the distal end of the push tube 313. An opening 3134 for communicating the exchange channel 3133 with the external environment is formed in the push tube 313. The operator can inject an injection such as liquid or gas into the body through the exchange channel 3133 to provide a drainage or exhaust function of the delivery system. Since the exchange channel 3133 is isolated from the tube cavity channel 3131, the exchange channel 3133 and the supporting member 316 in the tube cavity channel 3131 cannot affect each other; therefore, the drainage or exhaust function of the delivery system is guaranteed, and the proximal end of the delivery apparatus can also be ensured to have sufficient supporting force.

Figure 10:
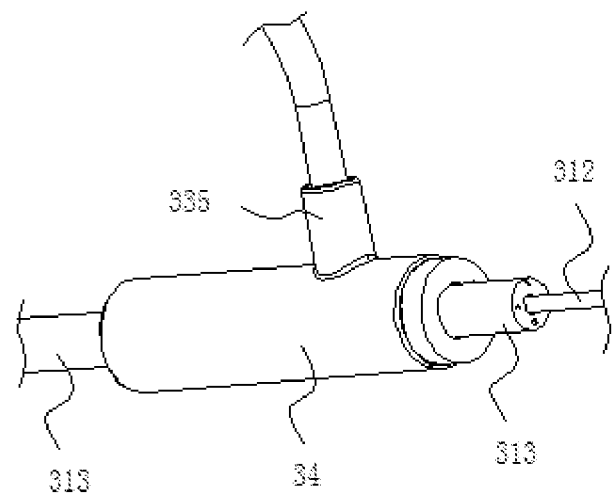
FIG. 10 is a three-dimensional diagram illustrating that the push tube joint of the joint assembly shown in FIG. 8 is connected with a communication tube.

The push tube joint 34 is approximately of a hollow structure, and is fixed outside the push tube 313. An exchange port 341 communicating with the opening 3134 is formed in the push tube joint 34. Referring to FIG. 9 and FIG. 10, one end of the communication tube 335 is connected to the push tube joint 34, and is communicated with the exchange port 341, and the other end extends out of the joint assembly. The operator can inject an injection such as liquid or gas into the exchange channel 3133 through the communication tube 335.

In the embodiment shown in FIG. 9, the push tube joint 34 surrounds the proximal end of the push tube 313; the exchange channel 3133 extends through two ends of the push tube 313 along the axial direction; the opening 3134 is formed in a side wall of the push tube 313; and the proximal end of the exchange channel 3133 is filled with a sealing member 343 to prevent the injection from flowing out from the proximal end of the push tube 313. The sealing member 343 may be glue or other fillers. An annular boss 345 communicating with the exchange port 341 is arranged on the push tube joint 34, and the communication tube 335 is in an inserted connection with the annular boss 345. In order to allow the injection to gently enter the exchange channel 3133, a transitional slot 342 is arranged on an inner wall of the push tube joint 34, and the transitional slot 342 is located between the opening 3134 and the exchange port 341. In order to prevent the injection from flowing into a gap between the push tube joint 34 and the push tube 313, a space between an edge of a notch of the transitional slot 342 and the push tube 313 is filled with a sealing member 343, and the sealing member 343 may be glue or other fillers. For the purpose of convenient machining, a proximal end of the transitional slot 342 extends to the proximal end of the push tube joint 34, and the proximal end of the push tube joint 34 is surrounded in a connection with a pressing block 344. The pressing block 344 is provided between the transitional slot 342 and the push tube 313 to seal the transitional slot 342 and the push tube 313 to prevent the injection from flowing out from the proximal end of the transitional slot 342.

It can be understood that the present embodiment does not define the specific position of the opening 3134 on the push tube 313 as long as the exchange channel 3133 is communicated with the communication tube 335. For example, in other embodiments, the opening 3134 may also be located on a proximal end surface of the push tube 313, and at this time, the communication tube 335 may be directly inserted into the opening 3134.

Figure 11:
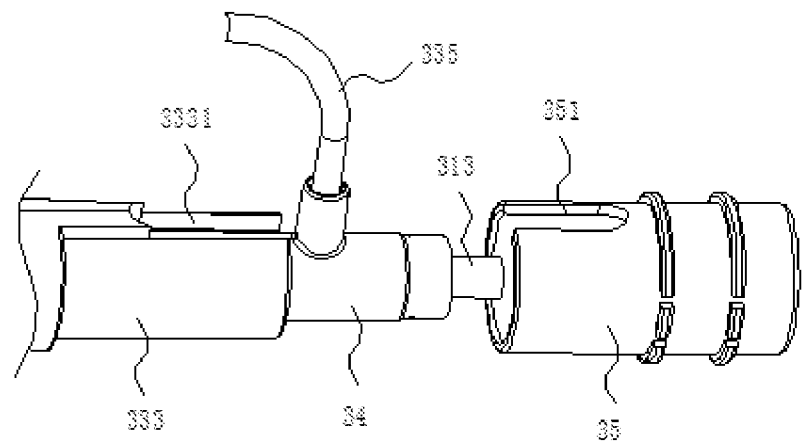
FIG. 11 is a schematic diagram of a push tube joint, a guide rod joint and a guide rod of the joint assembly shown in FIG. 8.
Figure 12:
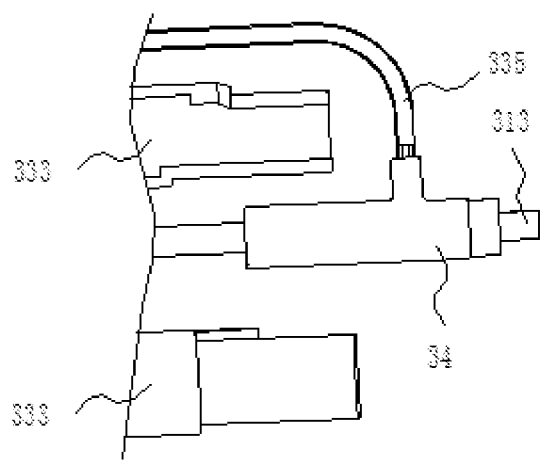
FIG. 12 is an exploded diagram of the guide rod shown in FIG. 11.

Referring to FIG. 11, the push tube joint 34 is inserted in the proximal end of the guide rod 333, and a communication tube fixing member 3331 is arranged on a side wall of the guide rod 333. The communication tube 335 passes through the communication tube fixing member 3331 and is connected to the push tube joint 34. In the embodiment shown in FIG. 12, the guide rod 333 is approximately of a cylindrical structure. The cylindrical structure is formed by splicing two semicircular connection cylinders, and the two connection cylinders can be spliced together via an adhesion or fastened connection. The communication tube fixing member 3331 is of a U-shaped slot structure, and is formed in a connection part of the two connection cylinders. A proximal end of the communication tube fixing member 3331 extends to the proximal end of the guide rod 333. When the push tube joint 34 is assembled in the guide rod 333, the side wall of the communication tube 335 abuts against a distal end of the communication tube fixing member 3331.

It can be understood that the present embodiment does not define the specific shape of the communication tube fixing member 3331 as long as the communication tube 335 can pass through it. For example, in other embodiments, the communication tube fixing member 3331 may also be of a round hole structure. The communication tube 335 passes through the communication tube fixing member 3331 and is connected to the exchange port 341 on the push tube joint 34. It can also be understood that the present embodiment does not define the specific structure of the guide rod 333 which can also be formed by splicing a plurality of connection cylinders.

Referring again to FIG. 11, the guide rod joint 35 is approximately of a hollow structure that can be surround and receive the guide rod 333. A communication tube positioning member 351 is arranged on the guide rod joint 35, and the communication tube 335 extends through the communication tube positioning member 351.

In the embodiment shown in FIG. 11, the communication tube positioning member 351 is of a U-shaped slot structure, a distal end of which extends to the distal end of the guide rod joint 35, and the side wall of the communication tube 335 abuts against a proximal end of the communication tube positioning member 351 when the guide rod joint 35 is assembled on the guide rod 333. It will be understood that the present embodiment does not define the specific shape of the communication tube positioning member 351 as long as the communication tube 335 can pass through it. For example, in other embodiments, the communication tube positioning member 351 may also be of a round hole structure.

It can be understood that since the communication tube 335 is connected to the push tube joint 34, if the communication tube 335 moves, the push tube joint 34 and the push tube 313 connected to the push tube joint 34 would move together, which is not good for accurate positioning of the tube cavity stent. The present embodiment can axially position the communication tube 335 by means of causing the communication tube 335 to abut against the proximal end of the communication tube positioning member 351 and causing the communication tube 335 to abut against the distal end of the communication tube fixing member 3331, thereby avoiding an axial movement of the communication tube 335. Further, in order to avoid a circumferential movement of the communication tube 335, the width of the communication tube fixing member 3331 or the communication tube positioning member 351 in a circumferential direction is the same as an outer diameter of the communication tube 335 located therebetween.

Since the guide rod joint 35 receives the guide rod 333, a first positioning structure (not shown) is arranged between the guide rod joint 35 and the guide rod 333 in order to prevent a relative movement between the guide rod joint 35 and the guide rod 333. The first positioning structure may include a clamping slot arranged on an inner wall of the guide rod joint 35, and a fastener arranged on an outer wall of the guide rod 333; and when the guide rod 333 is inserted into the guide rod joint 35, the fastener is fastened with the clamping slot to avoid a movement between the guide rod joint 35 and the guide rod 333. It can be understood that the present embodiment does not define the specific structure of the first positioning structure as long as the relative movement between the guide rod joint 35 and the guide rod 333 can be avoided.

Figure 13:
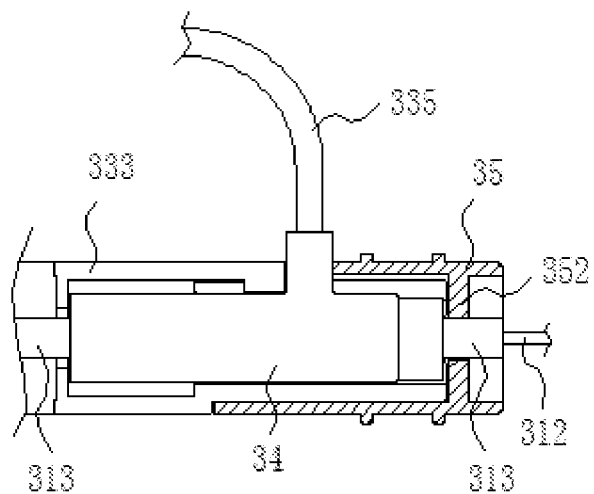
FIG. 13 is a sectional view illustrating that the push tube joint, the guide rod joint and the guide rod shown in FIG. 11 are connected.

Referring to FIG. 13, an annular clamping boss 352 protrudes from the inner wall of the guide rod joint 35, and the push tube 313 extends through the push tube joint 34 and the annular clamping boss 352 and extends to or near the proximal end of the guide rod joint 35. When the guide rod joint 35 receives the push tube joint 34, the proximal end of the push tube joint 34 abuts against the annular clamping boss 352. The annular clamping boss 352 can not only limit the axial movement of the push tube joint 34, but also support the push tube 313.

Figure 14:
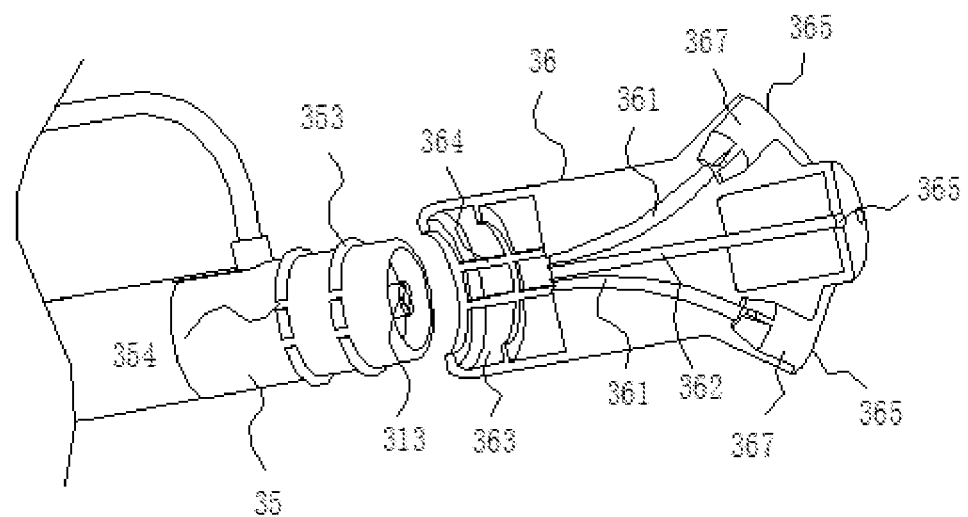
FIG. 14 is a schematic diagram of a guide rod joint and a guide wire joint shown in FIG. 8.
Figure 15:
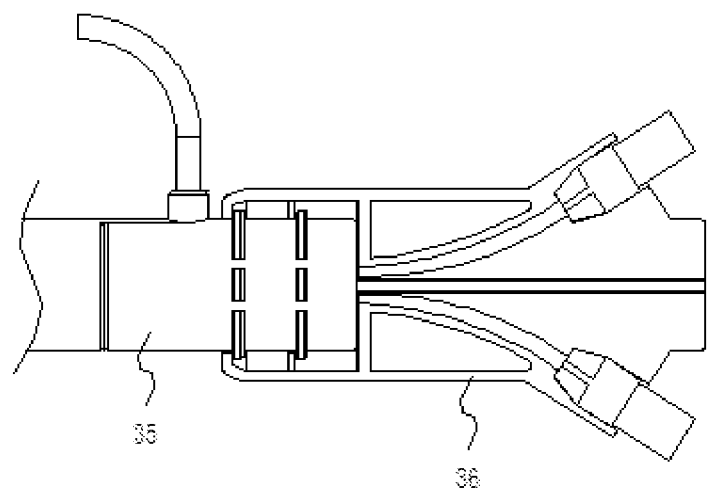
FIG. 15 is a schematic diagram illustrating that the guide rod joint and the guide wire joint shown in FIG. 14 are connected.
Figure 16:
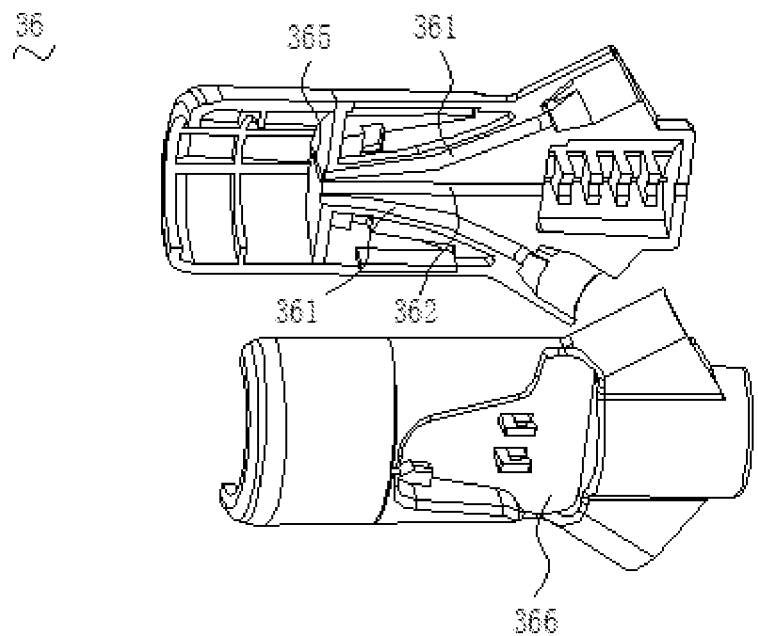
FIG. 16 is an exploded diagram of the guide wire joint shown in FIG. 8.

Referring to FIG. 14, FIG. 15 and FIG. 16, the guide wire joint 36 is approximately of a hollow structure, which surrounds and receives the guide rod joint 35. The push tube 313 is communicated with an inner cavity of the guide wire joint 36. A plurality of through holes 365 communicating with the inner cavity of the guide wire joint are formed in the guide wire joint 36, and a guide wire (the preset guide wire 15 or the limiting guide wire 21) extending out of the proximal end of the push tube 313 and the outer core tube 312 respectively extend out of the guide wire joint 36 through the corresponding through holes 365.

In order to facilitate the operator to move the guide wires and the outer core tube 312, an inner surface of the guide wire joint 36 is provided with a guide wire limiting slot 361 and a core tube limiting slot 362; and the guide wire extending out of the proximal end of the push tube 313 passes through the corresponding through hole 365 from the guide wire limiting slot 361, and the outer core tube 312 extending out of the proximal end of the push tube 313 passes through the corresponding through hole 365 from the core tube limiting slot 362.

In the embodiments shown in FIG. 14, FIG. 15 and FIG. 16, the proximal end of the push tube 313 extends into the guide wire joint 36, and one core tube limiting slot 362 and two guide wire limiting slots 361 are formed in the guide wire joint 36; and the two preset guide wires 15 are respectively mounted in the corresponding guide wire limiting slots 361. The core tube limiting slot 362 is distributed in the axial direction of the outer core tube 312, and the two guide wire limiting slots 361 are approximately arc-shaped and are respectively arranged at two sides of the inner core tube limiting slot 362. A guide wire locking apparatus 367 is arranged on a proximal end of the guide wire limiting slot 361, so that the guide wire is fixed in the guide wire joint 36 when the guide wire locking apparatus 367 is locked, and the guide wire can move relative to the guide wire joint 36 when the guide wire locking apparatus 367 is unlocked.

It can be understood that if an included angle between a connecting line between the proximal end and the distal end of the guide wire limiting slot 361 and a longitudinal central axis of the push tube 313 is larger, pushing resistance for the guide wire will be higher, which is not good for pushing and pulling the guide wire. However, if the above included angle is smaller, the guide wire can interfere more easily with other parts at the proximal end side of the guide wire joint 36. Therefore, in the present embodiment, when the guide wire joint 36 is received over the guide rod joint 35, the included angle between the connecting line between the proximal end and the distal end of the guide wire limiting slot 361 and the longitudinal central axis of the push tube 313 is between 20 degrees to 40 degrees.

It can also be understood that due to relatively low hardness of the guide wire, if there is a clearance between the proximal end of the push tube 313 and the distal end of the guide wire limiting slot 361, the guide wire can easily bend at this clearance in a forward pushing process, which affects the pushing of the guide wire. Therefore, in the present embodiment, when the guide wire joint 36 is received over the guide rod joint 35, the proximal end of the guide wire channel 3132 in the push tube 313 and the distal end of the guide wire limiting slot 361 are coaxial, and the proximal end surface of the push tube 313 and the distal end surface of the guide wire limiting slot 361 are located in the same plane.

Further, a second positioning structure is arranged between the guide wire joint 36 and the guide rod joint 35 to avoid a relative movement occurring between the guide wire joint 36 and the guide rod joint 35.

The second positioning structure includes first positioning slots 363 arranged on the inner wall of the guide wire joint 36, and first positioning ribs 353 arranged on an outer wall of the guide rod joint 35 and distributed in the circumferential direction. When the guide wire joint 36 is received over the guide rod joint 35, the first positioning ribs 353 are clamped in the first positioning slots 363 to avoid an axial movement occurring between the guide wire joint 36 and the guide rod joint 35. The second positioning structure further includes second positioning ribs 364 arranged on the inner wall of the guide wire joint 36 and distributed in the axial direction, and second positioning slots 354 arranged on the guide rod joint 35. The second positioning slots 354 are gaps formed in the first positioning ribs 353. When the guide wire joint 36 is received over the guide rod joint 35, the second positioning ribs 364 are clamped in the second positioning slots 354 to avoid a circumferential movement occurring between the guide wire joint 36 and the guide rod joint 35. During assembly, only the second positioning ribs 364 are inserted into the second positioning slots 354 until the first positioning ribs 353 are clamped into the first positioning slots 363 to realize axial and circumferential positioning of the guide wire joint 36 and the guide rod joint 35, so that the operation is simple and the machining is convenient. It can be understood that the present embodiment does not define the specific structure of the second positioning structure as long as no relative movement occurs between the guide wire joint 36 and the guide rod joint 35.

Figure 17:
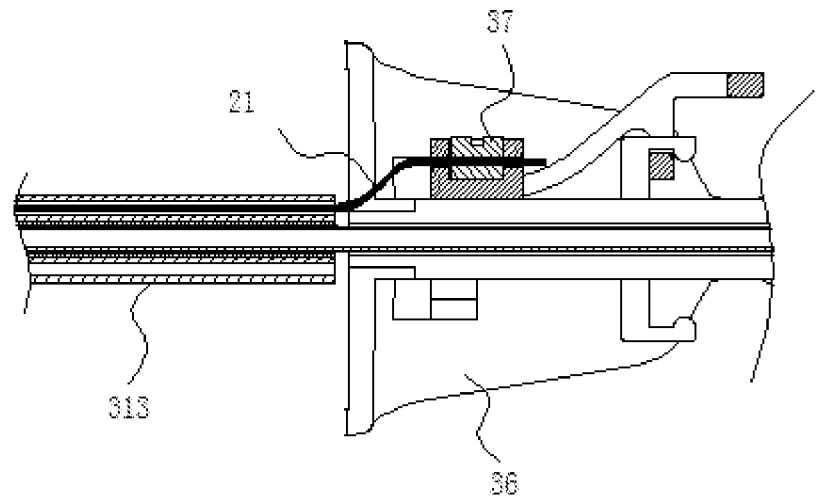
FIG. 17 is a sectional view of a guide wire positioning mechanism of the guide wire joint shown in FIG. 16.
Figure 18:
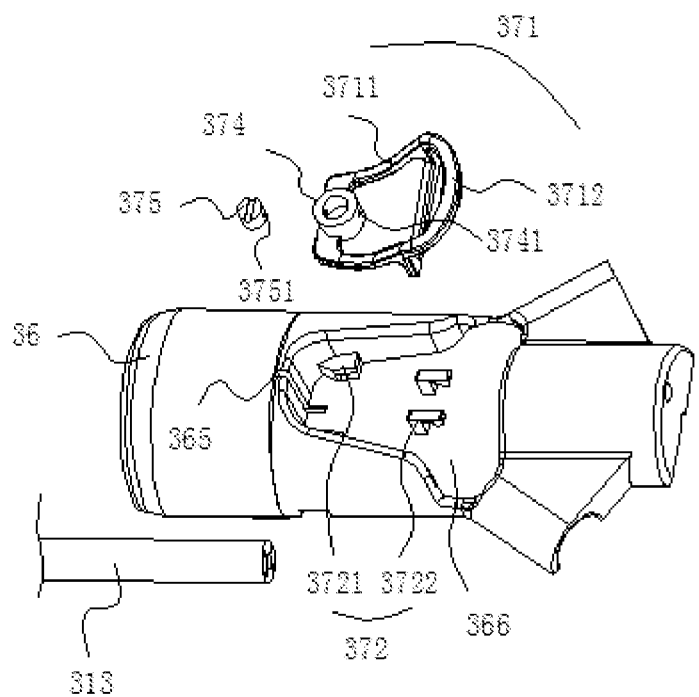
FIG. 18 is an exploded diagram of the guide wire positioning mechanism shown in FIG. 17.

Referring to FIG. 16, FIG. 17 and FIG. 18, a guide wire positioning mechanism 37 is also arranged on the guide wire joint 36. The guide wire (the limiting guide wire 21 or the preset guide wire 15) extending through the through hole 365 of the guide wire joint 36 is fixedly connected to the guide wire positioning mechanism 37. The guide wire positioning mechanism 37 causes the guide wire to be fixed on the guide wire joint 36 to avoid the guide wire from moving during the delivery process.

In the embodiment shown in FIG. 18, an outer surface of the guide wire joint 36 is provided with an accommodation slot 366, and the guide wire positioning mechanism 37 is mounted in the accommodation slot 366. The guide wire positioning mechanism 37 includes a pull fastener assembly 371, and a pull fastener positioning assembly 372 for limiting the pull fastener assembly 371. The guide wire is fixed on the pull fastener assembly 371, and the pull fastener assembly 371 is detachably connected to the pull fastener positioning assembly 372.

The pull fastener assembly 371 includes a pull fastener main body 3711, and a pull ring 3712 connected to the pull fastener main body 3711. After extending through the through hole 365, the limiting guide wire 21 is fixedly connected to the pull fastener main body 3711. The operator can put a finger into the pull ring 3712 to pull out the pull fastener assembly 371 from the pull fastener positioning assembly 372.

Figure 19:
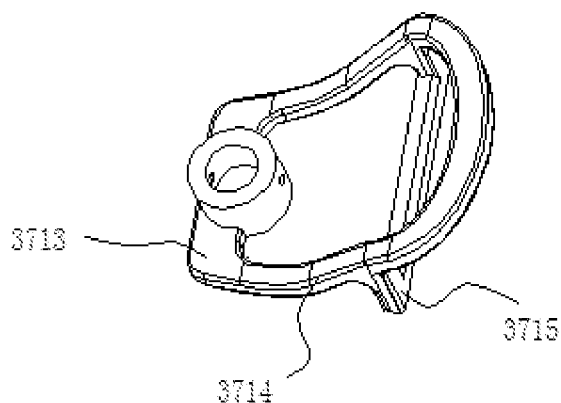
FIG. 19 is a schematic diagram of a pull fastener assembly of the guide wire positioning mechanism shown in FIG. 18.

Referring to FIG. 18 and FIG. 19, the pull fastener main body 3711 includes a first fastening portion 3713, a connection portion 3714 and a second fastening portion 3715. The first fastening portion 3713 is flat, and is approximately parallel to the plane of the bottom of the accommodation slot 366. One end of the connection portion 3714 is connected to the first fastening portion 3713, and the other end extends towards a side away from the accommodation slot 366; the pull ring 3713 is fixed at the other end of the connection portion 3714, so that a certain distance is reserved between the pull ring 3713 and the bottom of the accommodation slot, and the operator conveniently puts a finger into the pull ring 3713. The second fastening portion 3715 is fixed at the other end of the connection portion 3714, and extends towards a side close to the accommodation slot 366. The second fastening portion 3715 is flat, and approximately extends in a direction perpendicular to the bottom of the accommodation slot 366. A clamping slot structure is arranged on the second fastening portion 3715.

The pull fastener positioning assembly 372 includes a first positioning member 3721 and a second positioning member 3722. The first positioning member 3721 is approximately flat, and is fixed on a side wall of the accommodation slot 366. The second positioning member 3722 is provided with a fastener structure, and is fixed at the bottom of the accommodation slot 366. When the pull fastener assembly 371 is mounted in the accommodation slot 366, the first fastening portion 3713 is located below the first positioning member 3721, and abuts against the side wall of the accommodation slot 366. The fastener structure of the second positioning member 3722 is fastened with the clamping slot structure on the second fastening portion 3715 to limit the pull fastener assembly 371 on the guide wire joint 36.

The pull fastener assembly 371 further includes a fixing slot 374 arranged on the pull fastener main body 3711, and a fixing member 375 arranged in the fixing slot 374. During assembly, the limiting guide wire 21 is fixed on the fixing member 375, and then the fixing member 375 is assembled in the fixing slot 374, so that the fixing member 375 is fixedly mounted in the fixing slot 374. Since the guide wire has a smaller wire diameter, it is difficult to directly fix the guide wire on the pull fastener assembly 371. Through the structures of the fixing slot and the fixing member, the stability of the connection between the guide wire and the pull fastener assembly 371 can be strengthened.

Specifically, the fixing member 375 is approximately a cylindrical mechanism. A first guide channel 3751 extending in a radial direction is arranged on a side wall of the fixing member 375, and a second guide channel 3741 communicating with the first guide channel 3751 is arranged on a side wall of the fixing slot 374. During assembly, the proximal end of the guide wire extends through the first guide channel 3751 and the second guide channel 3741 to fix the guide wire on the fixing member 375.

It can be understood that, in other embodiments, the guide wire joint 36 may be provided with no accommodation slot 366 either, and the guide wire positioning mechanism 37 is directly assembled on the outer wall of the guide wire joint 36. It can also be understood that the present embodiment does not define the specific structure of the guide wire positioning mechanism 37. In other embodiments, the guide wire positioning mechanism 37 can also be of other structures as long as it can limit the guide wires.

The various technical features of the above-described embodiments may be combined in any manner. In order to simplify the description, all possible combinations of the various technical features in the above-described embodiments are not described. However, the combinations of these technical features should be deemed as falling within the scope in this specification, as long as they are not contradictory.

The embodiments set forth above represent only a few implementation modes of the present application, which are described in more details and more specifically, but are not to be construed as limiting the patent scope of the present application. It should be noted that those of ordinary skill in the art can also make several modifications and improvements without departing from the concept of the present application, and these modifications and improvements all fall within the protection scope of the present application. Therefore, the protection scope of the patent of the present application shall be subject to the claims attached.

The invention claimed is:

1. A delivery system, comprising a tube cavity stent and a delivery apparatus, wherein the tube cavity stent includes a tubular main body, and at least one branch connected to the tubular main body, a preset guide wire is arranged in the branch; the delivery apparatus comprising a sheath assembly, a tip, and a handle assembly, the sheath assembly comprising an inner core tube, a push tube surrounding and receiving the inner core tube, and a sheath surrounding and receiving the push tube and capable of moving axially relative to the push tube, the tip being connected to a distal end of the inner core tube, the handle assembly being connected to a proximal end of the sheath, a tube cavity channel for the inner core tube extending through the push tube, a guide wire channel is provided in the push tube, the preset guide wire extends through the guide wire channel; a limiting mechanism is provided on the tip; and the limiting mechanism detachably connects the preset guide wire extending through the guide wire channel; the limiting mechanism and the preset guide wire have a first fitted state and a second fitted state, when the limiting mechanism and the preset guide wire are in a first fitted state, the limiting mechanism is in interference fit with the preset guide wire or the limiting mechanism can apply an elastic clamping force to the preset guide wire, so that a front end of the limiting guide wire is connected to the limiting mechanism, and the front end of the preset guide wire is fixed relative to the tip; under the action of an external force, when the limiting mechanism and the preset guide wire are in the second fitted state, the front end of the preset guide wire is separated from the limiting mechanism, the preset guide wire moves relative to the limiting mechanism; wherein the handle assembly comprises a guide wire joint fixed at a proximal end of the push tube, and the guide wire joint is provided with a plurality of through holes communicating with the push tube.

2. A delivery system, comprising a tube cavity stent and a delivery apparatus, the delivery apparatus is configured to deliver the tube cavity stent, wherein the tube cavity stent comprising a tubular main body, and a semi-releasing apparatus connected to a surface of the tubular main body, the semi-releasing apparatus comprising a limiting guide wire, and a restrain unit movably connected to the limiting guide wire and used for performing circumferential restraining on the tubular main body; the delivery apparatus comprising a sheath assembly, a tip, and a handle assembly, the sheath assembly comprising an inner core tube, a push tube surrounding and receiving the inner core tube, and a sheath surrounding and receiving the push tube and capable of moving axially relative to the push tube, the tip being connected to a distal end of the inner core tube, the handle assembly being connected to a proximal end of the sheath, a tube cavity channel for the inner core tube extending through the push tube, a guide wire channel is provided in the push tube, the limiting guide wire can run through the guide wire channel, the limiting guide wire can be used for movably connecting the restrain unit; a limiting mechanism is provided on the tip; and the limiting mechanism is used for detachably connecting a limiting guide wire extending through the guide wire channel; the limiting mechanism and the limiting guide wire have a first fitted state and a second fitted state, when the limiting mechanism and the limiting guide wire are in a first fitted state, the limiting mechanism is in interference fit with the limiting guide wire or the limiting mechanism can apply an elastic clamping force to the limiting guide wire, so that a front end of the limiting guide wire is connected to the limiting mechanism, and the front end of the limiting guide wire can be fixed relative to the tip; under the action of an external force, when the limiting mechanism and the limiting guide wire are in the second fitted state, the front end of the limiting guide wire is separated from the limiting mechanism, the limiting guide wire can move relative to the limiting mechanism;

wherein the handle assembly comprises a guide wire joint fixed at a proximal end of the push tube, and the guide wire joint is provided with a plurality of through holes communicating with the push tube.

3. The delivery system according to claim 2, wherein the sheath assembly further comprises a supporting member located in the tube cavity channel; and a length of the supporting member is not greater than a length of the push tube.

4. The delivery system according to claim 3, wherein the sheath assembly further comprises an outer core tube and a fixed anchor connected to a distal end of the outer core tube; the outer core tube is arranged between the inner core tube and the supporting member, and is capable of moving axially relative to the inner core tube; and the tip is provided with a fixed anchor limiting slot cooperating with the fixed anchor.

5. The delivery system according to claim 2, wherein the limiting mechanism is a limiting slot, and the limiting slot is in interference fit with the guide wire connected in the limiting slot.

6. The delivery system according to claim 2, wherein a guide wire limiting slot communicating with the guide wire channel and the through holes respectively and used for the guide wire to extend through is arranged in the guide wire joint.

7. The delivery system according to claim 6, wherein an included angle between a connecting line between a proximal end and a distal end of the guide wire limiting slot and a longitudinal central axis of the push tube is between 20 degrees to 40 degrees.

8. The delivery system according to claim 6, wherein a proximal end of the guide wire channel and the distal end of the guide wire limiting slot are coaxial, and a distal end surface of the guide wire limiting slot and a proximal end surface of the push tube are located in the same plane.

9. The delivery system according to claim 2, wherein the guide wire joint is provided with a guide wire positioning mechanism.

10. The delivery system according to claim 9, wherein the guide wire positioning mechanism comprises a pull fastener assembly used for fixedly connecting the guide wire extending through the through holes, and a pull fastener positioning assembly for limiting the pull fastener assembly; the pull fastener positioning assembly is arranged on an outer surface of the guide wire joint; and the pull fastener assembly is detachably connected to the pull fastener positioning assembly.

11. The delivery system according to claim 10, wherein the outer surface of the guide wire joint is provided with an accommodation slot, and the pull fastener positioning assembly is mounted in the accommodation slot.

12. The delivery system according to claim 10, wherein the pull fastener assembly comprises a pull fastener main body fixedly connected to the guide wire, and a pull ring connected to the pull fastener main body.

13. The delivery system according to claim 12, wherein the pull fastener main body comprises a first fastening portion, a connection portion and a second fastening portion; one end of the connection portion is connected to the first fastening portion, and the other end of the connection portion extends towards a side away from the outer surface of the guide wire joint; the second fastening portion is connected to the other end of the connection portion and extends towards a side close to the outer surface of the guide wire joint; and the pull ring is connected to the other end of the connection portion.

14. The delivery system according to claim 12, wherein the pull fastener assembly further comprises a fixing slot arranged on the pull fastener main body, and a fixing member arranged in the fixing slot; and the fixing member is used for fixedly connecting the guide wire extending through the through holes.

15. A delivery system, comprising a tube cavity stent and a delivery apparatus, wherein the delivery apparatus comprising a sheath assembly, a tip, and a handle assembly, the sheath assembly comprising an inner core tube, a push tube surrounding and receiving the inner core tube, and a sheath surrounding and receiving the push tube and capable of moving axially relative to the push tube, the tip being connected to a distal end of the inner core tube, the handle assembly being connected to a proximal end of the sheath, a tube cavity channel for the inner core tube extending through the push tube, a guide wire channel is provided in the push tube; the tube cavity stent comprises a tubular main body, at least one branch connected to the tubular main body, and a semi-releasing apparatus connected to a surface of the tubular main body, the semi-releasing apparatus comprising a limiting guide wire, and a restrain unit movably connected to the limiting guide wire and used for performing circumferential restraining on the tubular main body, a preset guide wire is arranged in the branch, the preset guide wire and the limiting guide wire respectively run through the guide wire channel, and the preset guide wire and the limiting guide wire are detachably connected to a limiting mechanism; the limiting mechanism, the limiting guide wire and the preset guide wire have a first fitted state and a second fitted state, when the limiting mechanism, the limiting guide wire and the preset guide wire are in a first fitted state, the limiting mechanism is in interference fit with the limiting guide wire and the preset guide wire, or the limiting mechanism can apply an elastic clamping force to the limiting guide wire and the preset guide wire, so that front ends of the limiting guide wire and the preset guide wire are connected to the limiting mechanism, and the front ends of the limiting guide wire and the preset guide wire can be fixed relative to the tip; under the action of an external force, when the limiting mechanism, the limiting guide wire and the preset guide wire are in the second fitted state, the front ends of the limiting guide wire and the preset guide wire are separated from the limiting mechanism, the limiting guide wire and the preset guide wire can move relative to the limiting mechanism.

16. The delivery system according to claim 1, wherein the limiting mechanism is a limiting slot, and the limiting slot is in interference fit with the guide wire connected in the limiting slot.

17. The delivery system according to claim 1, wherein the sheath assembly further comprises a supporting member located in the tube cavity channel; and a length of the supporting member is not greater than a length of the push tube.

18. The delivery system according to claim 17, wherein the sheath assembly further comprises an outer core tube and a fixed anchor connected to a distal end of the outer core tube; the outer core tube is arranged between the inner core tube and the supporting member, and is capable of moving axially relative to the inner core tube; and the tip is provided with a fixed anchor limiting slot cooperating with the fixed anchor.

19. The delivery system according to claim 1, wherein the at least one branch comprises an inner branch, and the preset guide wire is provided within inner branch which is located inside the tubular main body.

* * * * *